(12) United States Patent
DeSantis

(10) Patent No.: US 10,004,628 B2
(45) Date of Patent: Jun. 26, 2018

(54) PREVENTING HUMAN INFANT OCCIPITAL PLAGIOCEPHALY

(71) Applicant: Stephanie L. DeSantis, Memphis, TN (US)

(72) Inventor: Stephanie L. DeSantis, Memphis, TN (US)

( * ) Notice: Subject to any disclaimer, the term of this patent is extended or adjusted under 35 U.S.C. 154(b) by 671 days.

(21) Appl. No.: 13/999,800

(22) Filed: Mar. 22, 2014

(65) Prior Publication Data

US 2015/0265452 A1  Sep. 24, 2015

(51) Int. Cl.
*A61F 5/37* (2006.01)

(52) U.S. Cl.
CPC ....................... *A61F 5/37* (2013.01)

(58) Field of Classification Search
CPC ......... A41B 13/00–13/08; A61F 5/37–5/3784; A61F 5/56; A47D 15/005–15/008; A41D 10/00; A41D 15/04; A41D 11/00; A47G 9/10–9/109
USPC ....................................................... 128/871
See application file for complete search history.

(56) References Cited

U.S. PATENT DOCUMENTS

| | | | |
|---|---|---|---|
| 5,007,412 A | 4/1991 | DeWall | |
| 5,362,304 A | 11/1994 | Vam | |
| 6,216,276 B1 * | 4/2001 | Eibert | A63B 71/146 2/161.2 |
| 6,473,923 B1 | 11/2002 | Straub | |
| 6,592,536 B1 | 7/2003 | Argenta | |
| 7,566,313 B1 | 7/2009 | Argenta | |
| 8,272,073 B2 | 9/2012 | Arensdorf et al. | |
| 8,332,978 B2 | 12/2012 | Wamock | |
| 2007/0163051 A1 | 7/2007 | Straub | |
| 2009/0217458 A1 | 9/2009 | Lord | |
| 2009/0222971 A1 * | 9/2009 | Chen | A47D 15/008 2/111 |
| 2011/0162660 A1 * | 7/2011 | Sanger | A61F 5/05891 128/873 |

OTHER PUBLICATIONS

Shapeguard Pillow; Tots 2 Be; www.babyflathead.org/shapeguard-pillow.
My Angel's Guardian, wavw.myangelsguardian.com/omdex/html.

* cited by examiner

*Primary Examiner* — Victoria J Hicks
*Assistant Examiner* — Michelle J Lee

(57) ABSTRACT

A method and orthotic for treating, substantially preventing, or minimizing the possibility of, human infant occipital plagiocephaly and sudden infant death syndrome (SIDS), utilizes or provides a garment dimensioned to fit a human infant. The garment (such as a vest or jacket) has an open top portion, a substantially closed front, a substantially closed rear, a first receptacle on the front, and a second receptacle on the rear and functionally cooperating with the first receptacle. Third and fourth receptacles are preferably also provided, the first and second receptacles on the left side of the garment, and the third and fourth on the right side. The garment may be primarily of a stretchable mesh fabric. A cylindrical or prismatic bolster (e. g. of firm foam or rubber) is provided in each of the first and second receptacles. The garment is placed on a human infant; and then the infant is laid on her/his side on a surface so that the bolsters substantially preclude the infant from rolling from her/his side onto her/his face or back on the surface.

20 Claims, 3 Drawing Sheets

PREVENTING HUMAN INFANT OCCIPITAL PLAGIOCEPHALY

BACKGROUND AND SUMMARY OF THE INVENTION

The invention relates to an orthotic and method for treatment of, substantially preventing, or minimizing the possibility of, human infant occipital plagiocephaly and sudden infant death syndrome (SIDS), serious problems.

In 1992 the American Academy of Pediatrics recommended placing infants on their backs for sleep to reduce the incidence of SIDS, and the technique was considered effective. However, the placement of infants on their backs for sleep also resulted in a significant increase in the incidence of deformational plagiocephaly (flattening of the head). Occipital plagiocephaly is a deformity that can develop when an infant preferentially sleeps in one position on the back of the head (occiput). The deformity that develops is varying degrees of flattening on one or both sides of the occiput. When unilateral, the entire skull base can be deformed into a parallelogram shape. The degree of severity can range from mild to a severe and disfiguring deformity. The incidence is estimated to be anywhere from 3-10 percent of all infants.

Side sleeping was originally considered acceptable as well in the prevention of SIDS. Positioners were created and made widely commercially available for use in side sleep positioning while preventing prone positioning, to thereby reduce the incidence of SIDS. These positioners were also useful in concept to prevent and treat occipital plagiocephaly. However, in 2012, the CDC published a report of thirteen infant deaths over a period of fourteen years associated with wedge or bolster side sleeping devices that were commercially available. This caused the FDA and the American Academy of Pediatrics (AAP) to recommend against the use of these devices. Furthermore, the AAP recommended against side positioning altogether because it was felt that side sleeping was an unstable position and that an infant was more likely to roll to a prone position (than to a supine position), and thus expose them to the risk of SIDS.

There has been really no physiologic reason shown that sleeping in the side position, per se, places an infant at risk for SIDS. It is only a risk because of the potential to allow the infant to roll to a prone position, or move/roll to a position that wedges the baby's face against something soft in the bed causing suffocation. The reason that unilateral plagiocephaly occurs in the first place is that the infant preferentially lies on one side of the occiput. Preventing the infant from preferentially lying on the developed flat side of the occiput is a logical, simple, and proven treatment for this deformity.

Reducing the incidence of preferential pressure applied to the one flat side of the head, (i.e., the force that created the deformity in the first place) allows the rapidly growing infant brain to push the skull out normally and unencumbered, and the deformity self corrects. Having the infant sleep preferentially on the unaffected side is a simple and effective treatment for occipital plagiocephaly, but it must be done safely. Historically, side sleeping positioners were effective in treating occipital plagiocephaly, especially in infants younger than four months who could not roll over well yet on their own. The reason the commercially available wedge or bolster side sleepers were deemed to be unsafe is because their design allowed the infant to still move around while in them. Apparently there were a few deaths identified where it was thought that the infant's face became wedged against the bolster and this caused suffocation.

According to the invention an orthotic and method are provided which allow positioning an infant for side sleeping for prevention or treatment of occipital plagiocephaly.

According to one aspect of the present invention there is provided an orthotic for treating, substantially preventing, or minimizing the possibility of, human infant occipital plagiocephaly and sudden infant death syndrome. The orthotic comprises: A garment having an open top portion, a substantially closed front with right and left sides, and a substantially closed rear with right and left sides, and dimensioned to fit a human infant. At least a first receptacle on the front of the garment. At least a second receptacle on the rear of the garment and operatively associated with the first receptacle. And, first and second bolsters positionable Within the first and second receptacles, respectively, and when positioned therein substantially precluding an infant wearing the garment from rolling over from her or his side to her or his face or back.

The first and second receptacles may be on the left side of the front and rear of the garment, and the garment desirably further comprises third and fourth receptacles on the right side of the front and rear, respectively, of the garment, for receiving one of the first and second bolsters therein. Preferably the bolsters are selected from the group consisting essentially of foam or rubber cylinders and prisms, e. g. having a durometer of between about 40-70 on the Shore A scale.

The garment may be primarily constructed of a stretchable mesh material/fabric. The garment may be selected from the group consisting essentially of a vest and jacket. Desirably the garment has fasteners along the front thereof facilitating placement of the garment on an infant.

The receptacles are desirably selected from the group consisting essentially of sleeves and pockets having fasteners which allow a bolster entry thereinto and removal therefrom. For example, the receptacles may comprise sleeves having open bottoms closed by flaps with fasteners associated therewith for closing the sleeves to retain bolsters therein.

According to another aspect of the present invention there is provided a method of treating, substantially preventing, or minimizing the possibility of human infant occipital plagiocephaly and sudden infant death syndrome, utilizing a garment dimensioned to fit a human infant and having an open top portion, a substantially closed front with right and left sides, a substantially closed rear with right and left sides, a first receptacle on the front, and a second receptacle on the rear operatively associated with the first receptacle. The method comprises: a) providing a bolster in each of the first and second receptacles; b) placing the garment on a human infant; and c) laying the infant on her or his side on a surface so that the bolsters substantially preclude the infant from rolling from her or his side onto her or his face or back on the surface.

In the practice of the method, desirably the first and second receptacles are on the garment left side and third and fourth receptacles are provided on the garment right side and all of the receptacles allow a bolster to be inserted thereinto, and removed therefrom. In such a situation, when c) is practiced to lay the infant on her or his left side a) is practiced to insert bolsters into the first and second receptacles, and to make the third and fourth receptacles bolster-free; and when c) is practiced to lay the infant on her or his right side then a) is practiced to insert bolsters into the third and fourth receptacles and to make the first and second receptacles bolster-free.

The garment used in the practice of the method may be a vest with fasteners closing an opening in the front thereof, and having arm openings, in which case b) is practiced by opening the front of the vest, placing the infant's arms in the arm holes and the infant's head in the open top portion, and closing the front of the vest with the fasteners.

According to yet another aspect of the present invention, a vest or jacket dimensioned to fit a human infant is provided, comprising: A garment having an open top, arm openings, an open front closed by fasteners, a substantially open bottom, and a closed rear. First and second receptacles provided on the front and rear of the left side of the garment. Third and fourth receptacles provided on the front and rear of the right side of the garment. First and second rubber or foam cylindrical or prismatic bolsters dimensioned to fit within the first and second receptacles, or the third and fourth receptacles, respectively. And wherein the receptacles are constructed to allow one of the bolsters to be inserted thereinto and removed therefrom.

The arm openings may be sleeveless so that the garment comprises a vest; and wherein the garment may be primarily constructed of stretchable mesh fabric. The receptacles may comprise sleeves with openings closeable by flaps with fasteners so that when the fasteners associated with a given sleeve and flap are unfastened a bolster can be inserted into that sleeve past that sleeve's flap.

It is the primary object of the present invention to provide an orthotic and method which allow positioning an infant for side sleeping for prevention, minimizing the possibility of, or treatment of occipital plagiocephaly. This and other objects of the invention will become clear from the detailed description of the drawings, and the appended claims.

DETAILED DESCRIPTION OF THE DRAWINGS

Figure 1:
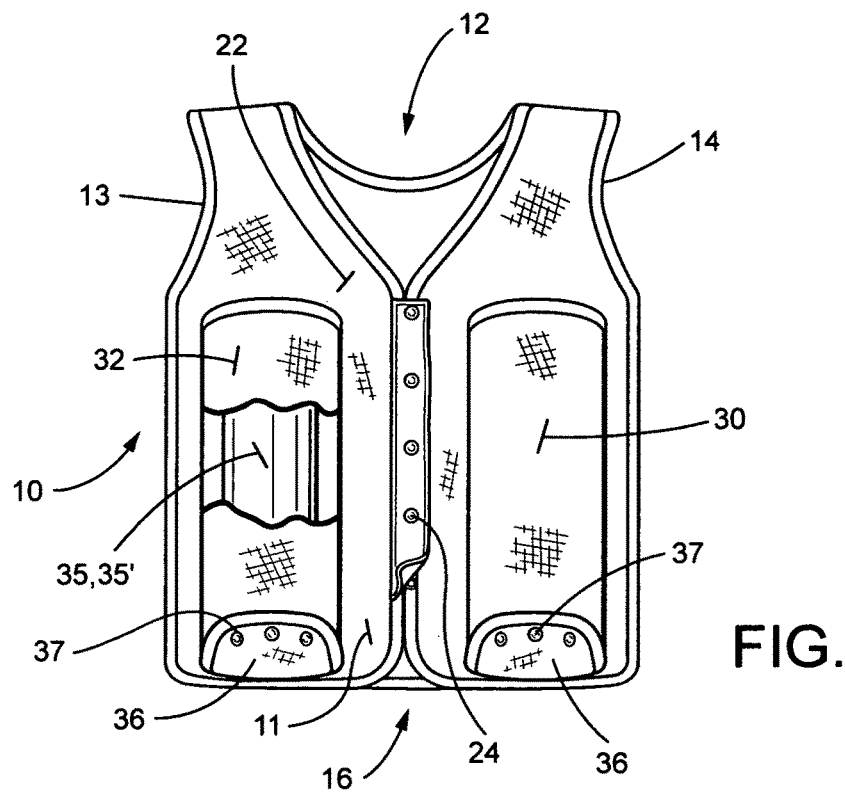
FIG. 1 is a front view of an exemplary orthotic according to the present invention.
Figure 2:
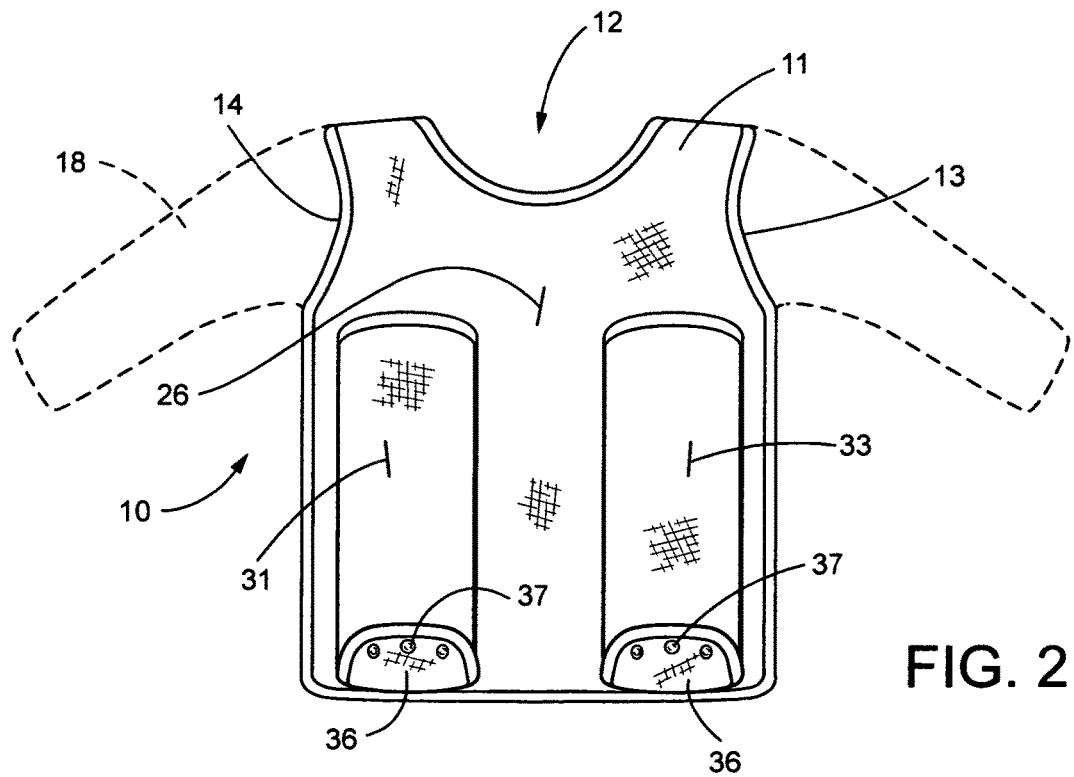
FIGS. 2 and 3 are rear and side views, respectively, of the orthotic of FIG. 1.
Figure 3:
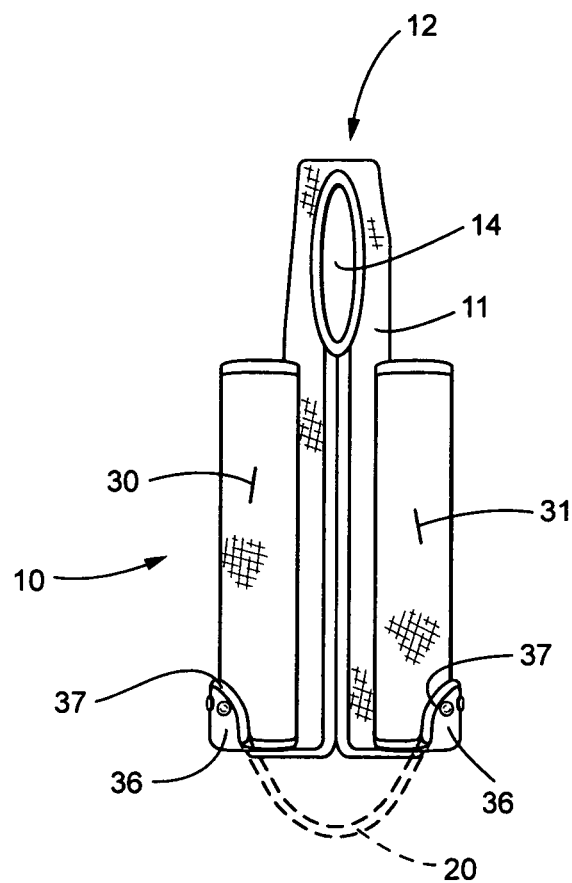

FIGS. 1-3 show an exemplary form of an orthotic 10 according to the present invention for treating, substantially preventing, or minimizing the possibility of, human infant occipital plagiocephaly and sudden infant death syndrome (SIDS). The orthotic is in the form of a garment 11. In the drawings in solid line the garment 11 is in the form of a vest having an open top 12 for an infant's neck and head, sleeveless arm holes 13, 14. and an open bottom 16. However it is to be understood that the garment 11 may be a jacket, including sleeves (such as shown at dotted line at 18 in FIG. 2), and instead of the bottom 16 being open it may include legs and feet, or a strap (shown in dotted line at 20 in FIG. 3) such as utilized in infant life vests, and the garment 11 may also have a hood.

The garment 11 is dimensioned to fit a human infant, typically a baby human between one and twelve months old, the age when SIDS is statistically most likely to occur.

While the garment/vest 11 may be a pull-over, for ease of fitting it on an infant desirably the front 22 thereof has a conventional opening closed by conventional fasteners (e. g. snap fasteners, hook and loop fasteners such as VELCRO®, or the like) shown schematically at 24 in FIG. 1. The rear 26 (FIG. 2) is desirably closed.

Figure 4:
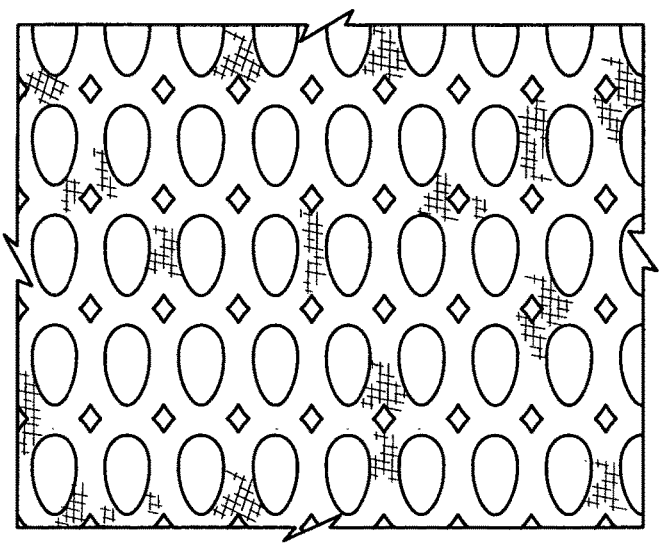
FIG. 4 is a plan view of part of an exemplary stretchable mesh fabric that may be used as the primary component of the orthotic of FIGS. 1-3.
Figure 5:
FIG. 5 is a side view of an exemplary bolster utilized according to the present invention.
Figure 6:
FIG. 6 is an end view of the bolster of FIG. 5.
Figure 7:
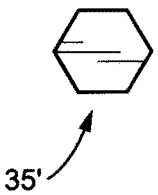
FIG. 7 is a view like that of FIG. 6 showing an alternative form of a bolster according to the invention, namely one comprising a hexagonal prism.

The garment 11 may be made of any suitable fabric material. One desirable fabric is a conventional stretchable mesh 28, shown schematically in FIG. 4, such as one made of nylon and spandex, although any other suitable materials may be utilized. The garment 11 need not be made entirely of stretchable mesh, but preferably is primarily of stretchable mesh. The sleeves 18 and strap 20, if provided, typically would not be of stretchable mesh, nor would legs and feet if utilized, but could be of cotton or other suitable material. The garment 11 may be treated with a conventional safe fire retardant.

The orthotic 10 also comprises at least a substantially vertical (considering the line from the open top 12 to the open bottom 16) first receptacle 30 on the front 22 of the garment 11, and at least a second substantially vertical receptacle 31 (see FIG. 2) on the rear 26 of the garment 11, the second receptacle 31 positioned so that it is operatively associated with the first receptacle 30, that is so that the receptacles 30, 31 functionally cooperate to prevent or minimize the possibility of an infant wearing the garment from rolling from her/his side to her/his face or back. In the preferred embodiment illustrated the first receptacle 30 is on one of the right and left sides (the left side in FIG. 1) of the front 22, and the second receptacle 31 is on the same side thereof as the first receptacle 30, although the receptacles 30, 31 could be located more centrally.

While just two receptacles 30, 31 may be utilized, especially if the garment 11 is reversible (such as if the front 22 and rear 26 are substantially the same so that the same receptacles can be used regardless of whether the infant wearing the garment 11 is on her or his left or right side), preferably third 32 and fourth 33 receptacles, substantially identical to the receptacles 30, 31, are provided on the right side (when the receptacles 30, 31 are on the left side) of the front 22 and rear 26, respectively, of the garment 11.

The receptacles 30-33 preferably are in the form of pockets or sleeves which are constructed so that a bolster 35, 35' (see FIGS. 1 and 5-7) may be inserted therein. In the exemplary embodiment illustrated in the drawings this is accomplished by providing the receptacles 30-33 as sleeves which are open at the bottoms thereof, and with the bottoms closed by flaps 36 having conventional fasteners shown schematically at 37 in FIGS. 1-3 associated therewith and with the sleeves 30-33 with which they cooperate. The fasteners 37 may be of any suitable conventional type, e. g. such as snap fasteners, hook and loop fasteners such as VELCRO®, or the like, and are provided both on a flap 36 and a sleeve 30-33 with which the flap cooperates.

First and second bolsters 35, 35' are positionable within either the first and second receptacles, 30, 31, or the third and fourth receptacles 32, 33, such as a bolster 35, 35' shown within the sleeve 32 in FIG. 1. When the bolsters 35, 35' are positioned in the receptacles 30, 31 or 32, 33, they substantially preclude, or greatly minimize the possibility of, an infant wearing the garment 11 from rolling over from her/his side to her/his face or back. This substantially prevents or minimizes the possibility of human infant occipital plagiocephaly and SIDS.

The bolster 35 (FIGS. 5 & 6) is shown as a cylinder, and the bolster 35' (FIG. 7) is shown as a prism (in this case a hexagonal prism). The cylinders 35 may be circular or elliptical in cross-section, and the prisms 35' may have any polygonal shape in cross-section, including triangle, rectangle, rhombus, trapezoid, pentagon, octagon, etc.

The bolsters 35, 35' may be made of any suitable material that is sufficiently firm to provide the desired roll-preventing function thereof, yet is soft enough not to injure the infant using the garment 11. For example the bolsters 35, 35' may be made of rubber or foam having a durometer of between about 40-70 (e. g. 50-60) on the Shore A scale. Thus the bolsters 35, 35' will be of a relatively stiff rubber or foam material, which will help keep the garment 11 from riding up to encroach upon the infant's face. The armholes 13, 14 will help prevent upward migration of the garment 11 as well.

While any suitable material could be used for bolsters 35, 35', silicone foam and closed cell polyurethane foam may be desirable.

The lengths and diameters (or other largest cross-sectional dimension) of the bolsters 35, 35' may vary depending upon the size of the infant that the garment 11 is designed to fit. A typical length of a bolster 35, 35' is about seven-twelve inches, and a typical diameter or other largest cross-sectional dimension is about two-five inches.

The orthotic 10 is typically sized and fit to a particular infant by a trained, licensed professional (preferentially a physical therapist), thus reducing the possibility of a poorly fitting orthotic.

In a typical method of use of a properly fitted and sized orthotic 10 for treating, substantially preventing, or minimizing the possibility of, human infant occipital plagiocephaly and SIDS, the garment 11 is placed on a surface with the rear 26 thereof engaging the surface. The fasteners 24 are unfastened to allow ready access to the interior of the garment. The infant is placed within the garment 11 on her/his back through the open front 22 of the garment 11, and her/his arms are placed through the arm holes 13, 14 with her/his head extending outwardly from the top opening 12. The fasteners 24 are then re-fastened to close the front 22.

If the bolsters 35 (or 35') are not already in the appropriate sleeves 30-33 they are placed therein. Assuming that at this time that it is desirable for the infant to lay on her/his left side and the bolsters 35 are not already in place then the fasteners 37 associated with each of the bottom flaps 36 of each of the sleeves 30, 31 are unfastened and a bolster 35 is slid into each sleeve 30, 31. Then the fasteners 37 for both flaps 36 are re-fastened (the sleeves 32, 33 in this case are devoid of a bolster 35). Then the infant is laid on her/his left side in her/his crib or on any other desired surface. The bolsters 35 substantially preclude the infant from rolling over from her/his side to her/his face or back.

Which side the infant will be placed on will, of course, be determined by whether the infant is being treated for existing occipital plagiocephaly. The infant will be placed on her/his opposite side from her/his side exhibiting occipital plagiocephaly. For prevention, the infant will be placed on alternating sides for alternating times (e. g. right side one day, left side the next).

While the invention has been shown and described in a practical and preferred embodiment thereof it is to be understood that many other modifications are possible within the scope of the invention. Also, any numerical ranges given are to be interpreted to include all individual ranges therewithin; for example "about seven-twelve inches" means 6.9-11.1 inches, 9.8-12.1 inches, 10.2-11.3 inches, and all other narrower ranges within the broad range. The invention is to be given the broadest interpretation of the appended claims, limited only by the prior art, so as to encompass all equivalent methods and devices.

What is claimed is:

1. An orthotic for treating, substantially preventing, or minimizing the possibility of, human infant occipital plagiocephaly and sudden infant death syndrome, comprising:
    a garment having an open top portion, a substantially closed front with right and left sides, and a substantially closed rear with right and left sides, and dimensioned to fit a human infant;
    at least a first receptacle on said front of said garment;
    at least a second receptacle on said rear of said garment and operatively associated with said first receptacle; and
    first and second bolsters positionable within said first and second receptacles, respectively, and when positioned therein substantially precluding, or minimizing the possibility of, an infant wearing said garment from rolling over from her or his side to her or his face or back.

2. An orthotic as recited in claim 1 wherein said first and second receptacles are on said left side of said front and rear of said garment; and further comprising third and fourth receptacles on said right side of said front and rear, respectively, of said garment, for receiving one of said first and second bolsters therein.

3. An orthotic as recited in claim 2 wherein said bolsters are selected from the group consisting essentially of foam or rubber cylinders and prisms.

4. An orthotic as recited in claim 3 wherein said garment is primarily of a stretchable mesh material.

5. An orthotic as recited in claim 4 wherein said garment is selected from the group consisting essentially of a vest and jacket.

6. An orthotic as recited in claim 5 wherein said receptacles are selected from the group consisting essentially of sleeves and pockets having fasteners which allow the bolsters entry thereinto and removal therefrom.

7. An orthotic as recited in claim 3 wherein said bolsters comprise foam or rubber having a durometer of between about 40-70 on the Shore A scale.

8. An orthotic as recited in claim 2 wherein said receptacles are selected from the group consisting essentially of sleeves and pockets which allow the bolsters entry thereinto and removal therefrom.

9. An orthotic as recited in claim 1 wherein said garment is primarily of a stretchable mesh material.

10. An orthotic as recited in claim 1 wherein said garment is selected from the group consisting essentially of a vest and jacket.

11. An orthotic as recited in claim 1 wherein said bolsters are selected from the group consisting essentially of foam or rubber cylinders and prisms having a durometer of between about 40-70 on the Shore A scale.

12. An orthotic as recited in claim 1 wherein said garment has fasteners along the front thereof facilitating placement of said garment on said infant.

13. An orthotic as recited in claim 1 wherein said receptacles comprise sleeves having open bottoms closed by flaps with fasteners associated therewith for closing said sleeves to retain bolsters therein.

14. An orthotic for treating, substantially preventing, or minimizing the possibility of, human infant occipital plagiocephaly and sudden infant death syndrome, comprising: a garment primarily of stretchable mesh material having an open top portion, a substantially closed front with right and left sides, and a substantially closed rear with right and left sides, and dimensioned to fit a human infant; at least a first receptacle external of said front of said garment; at least a second receptacle external of said rear of said garment and operatively associated with said first receptacle; and first and second bolsters positionable within said first and second receptacles, respectively, and when positioned therein substantially precluding, or minimizing the possibility of, said infant wearing said garment from rolling over from her or his side to her or his face or back.

15. An orthotic as recited in claim 14 wherein said first and second receptacles are external of said front and rear of said garment on said left side of said front and rear of said garment; and further comprising third and fourth receptacles external of said front and rear of said garment on said right side of said front and rear, respectively, of said garment, for receiving one of said first and second bolsters therein.

16. An orthotic as recited in claim 15 wherein two bolsters are in combination with said garment in receptacles, and said bolsters are provided in only one of said first and second receptacles, or said third and fourth receptacles.

17. An orthotic as recited in claim 14 wherein said garment has fasteners along substantially the entire front thereof and substantially parallel to said first receptacle so as to facilitate placement of said garment on said infant.

18. An orthotic as recited in 14 wherein said receptacles comprise sleeves having an opening closed by flaps with fasteners associated therewith for closing said sleeves to retain bolsters therein.

19. An orthotic for treating, substantially preventing, or minimizing the possibility of, human infant occipital plagiocephaly and sudden infant death syndrome, comprising: a garment having an open top portion, a substantially closed front with right and left sides, and a substantially closed rear with right and left sides, and dimensioned to fit a human infant; at least a first receptacle external of said front of said garment; at least a second receptacle external of said rear of said garment and operatively associated with said first receptacle; first and second bolsters positionable within said first and second receptacles, respectively; and fasteners along substantially the entire front thereof and substantially parallel to said first receptacle so as to facilitate placement of said garment on said infant.

20. An orthotic as recited in claim 19 wherein said first and second receptacles are external of said front and rear of said garment on said left side of said front and rear of said garment; and further comprising third and fourth receptacles external of said front and rear of said garment on said right side of said front and rear, respectively, of said garment, for receiving one of said first and second bolsters therein.

* * * * *